United States Patent [19]

Lüthy et al.

[11] Patent Number: 4,788,210

[45] Date of Patent: Nov. 29, 1988

[54] 1,2,4-TRIAZOLE COMPOUNDS

[75] Inventors: Christoph Lüthy, Schwerzenbach; René Zurflüh, Bülach, Switzerland

[73] Assignee: Hoffmann-La Roche Inc., Nutley, N.J.

[21] Appl. No.: 808,962

[22] Filed: Dec. 16, 1985

[30] Foreign Application Priority Data

Dec. 21, 1984 [CH] Switzerland .......................... 6105/84
Sep. 25, 1985 [CH] Switzerland .......................... 4151/85

[51] Int. Cl.$^4$ .................. A01N 43/653; C07D 249/08
[52] U.S. Cl. ..................................... 514/383; 548/262; 546/276
[58] Field of Search ......................... 548/262; 514/383

[56] References Cited

U.S. PATENT DOCUMENTS 4,097,599  6/1978  Evans et al. ........................ 548/262
4,119,635 10/1978  Omodei-Sale et al. ............. 548/262
4,414,221 11/1983  Parsons et al. ...................... 548/262

OTHER PUBLICATIONS

Hinman et al., J. Am. Chem. Soc. 80:1895 (1958).
Lin et al., J. Het. Chem. 20:1693 (1983).
Lin et al., J. Het. Chem. 19:613 (1982).

*Primary Examiner*—Glennon H. Hollrah
*Assistant Examiner*—Patricia L. Morris
*Attorney, Agent, or Firm*—Jon S. Saxe; George M. Gould; Norman C. Dulak

[57] ABSTRACT

The invention is concerned with novel heterocyclic compounds of the formula

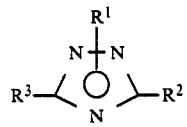

I wherein $R^1$, $R^2$ and $R^3$ are as hereinafter set forth, and their acid addition salts, processes for the preparation of these compounds, pest control compositions which contain these compounds as the active substance, as well as the methods of use of such compounds or compositions for the control of pests.

16 Claims, No Drawings

1,2,4-TRIAZOLE COMPOUNDS

DETAILED DESCRIPTION OF THE INVENTION

The invention is concerned with heterocyclic compounds, namely 1,2,4-triazoles of the general formula

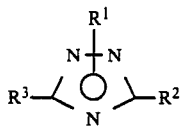

I wherein
R[1] is attached to the 1- or 2-positioned of the 1,2,4-triazole ring and is $C_{1-4}$-alkyl, $C_{1-4}$-haloalkyl or $C_{2-4}$-alkenyl,
R[2] is phenyl which is substituted with 1 to 3 chlorine, bromine and/or iodine atoms, 1 to 5 fluorine atoms, 1 or 2 $C_{1-4}$-alkyl groups, 1 or 2 halomethyl groups, 1 or 2 $C_{1-2}$-alkoxy groups, 1 or 2 $C_{1-2}$-haloalkoxy groups, a methylthio group, a cyano grup and/or a nitro group; or 2-, 3- or 4-pyridyl which is optionally substituted with 1 to 3 chlorine atoms and/or a methyl group
and R[3] is o-trifluoromethyl-phenyl or 4-trifluoromethyl-3-pyridyl,
and acid addition salts of these compounds.

Formula I is accordingly intended to embrace the compounds of the general formulae

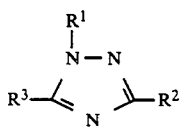

Ia and

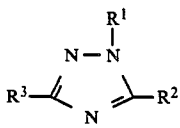

Ib

The compounds of formula I and their acid addition salts are pest control agents and are especially suitable for the control of insects and mites, e.g. spider mites. Accordingly, the invention also embraces pest control compositions which contain compounds of formula I or acid addition salts thereof as the active substance, processes for the preparation of these compounds as well as methods of use of these compounds or compositions for the control of pests.

The $C_{1-4}$-alkyl residues ad $C_{2-4}$-alkenyl residues referred to in the above definition of the compounds of formula I can be not only straight-chain but also branched. This also applies to the alkyl part of the $C_{1-4}$-haloalkyl group.

The term "halogen" embraces fluorine, chlorine, bromine and iodine. The groups "$C_{1-4}$-haloalkyl" "halomethyl" and "$C_{1-2}$-haloalkyl" can each have one or more halogen substituents, which can be the same of different. The substituents on the phenyl residue can also be the same or different.

Having regard to the presence of one or more asymmetric carbon atoms in the compounds of formula I the compounds occur in optically active form. Formula I is accordingly intended to embrace the racemates as well as the separated optically active forms.

As acid addition salts of the compounds of formula I there come into consideration physiologically compatible salts, such as salts of these compounds with strong acids, preferably hydrohalic acids, e.g. hydrochloric and hydrobromic acids; nitric acid; phosphoric acid; and sulfuric acid.

An interesting sub-group of compounds of formula I comprises those compounds of formula I in which R[1] is as defined above, R[2] is phenyl which is substituted with 1 to 3 fluorine, chlorine, bromine and/or iodine atoms, 1 or 2 $C_{1-4}$-alkyl groups, 1 or 2 trifluoromethyl groups, 1 or 2 $C_{1-2}$-alkoxy groups, a methylthio group, a cyano group and/or a nitro group or 2-, 3- or 4-pyridyl which is optionally substituted with 1 to 3 chlorine atoms and/or a methyl group and R[3] is o-trifluoromethyl-phenyl.

R[1] is preferably situated in the position adjacent to the group R[3], i.e. the compounds of formula Ia are preferred to those of formula Ib.

Independently of one another R[1] is preferably $C_{1-4}$-alkyl, especially methyl or ethyl, and R[2] is preferably substituted phenyl which has at least one substituent in an ortho-position, especially an ortho-halogen atom. R[2] is most preferably o-halophenyl, o,o'-dihalophenyl or o,p-dihalophenyl.

Especially preferred compounds of formula I are:
3-(o-Chlorophenyl)-1-methyl-5-(o-trifluoromethyl-phenyl)-1H-1,2,4-triazole and mixtures of this compound with 5-(o-chlorophenyl)-1-methyl-3-(o-trifluoromethyl-phenyl)-1H-1,2,4-triazole, 3-(o,o'-difluorophenyl)-1-methyl-5-(o-trifluoromethyl-phenyl)-1H-1,2,4-triazole and mixtures of this compound with 5-(o,o'-difluorophenyl)-1-methyl-3-(o-trifluoromethyl-phenyl)-1H-1,2,4-triazole, 3-(o-bromophenyl)-1-methyl-5-(o-trifluoromethyl-phenyl)-1H-1,2,4-triazole, 3-(2-chloro-6-fluorophenyl)-1-methyl-5-(o-trifluoromethyl-phenyl)-1H-1,2,4-triazole, 3-o,p-dichlorophenyl)-1-methyl-5-(o-trifluoromethyl-phenyl)-1H-1,2,4-triazole and 3-(2-chloro-4-fluorophenyl)-1-methyl-5-(o-trifluoromethyl-phenyl)-1H-1,2,4-triazole.

Other preferred compounds of formula I are:
3-(o-Iodophenyl)-1-methyl-5-(o-trifluoromethyl-phenyl)-1H-1,2,4-triazole, 3-(o,p-difluorophenyl)-1-methyl-5-(o-trifluoromethyl-phenyl)-1H-1,2,4-triazole, 3-(o-chlorophenyl)-1-methyl-5-(4-trifluoromethyl-3-pyridyl)-1H-1,2,4-triazol, 3-(o-fluorophenyl)-1-methyl-5-(o-trifluoromethyl-phenyl)-1H-1,2,4-triazole, 1-ethyl-3-(o-chlorophenyl)-5-(o-trifluoromethyl-phenyl)-1H-1,2,4-triazole, 1-ethyl-3-(o,i'-difluorophenyl)-5-(o-trifluoromethyl-phenyl)-1H-1,2,4-triazole and 3-(o-cyanophenyl)-1-methyl-5-(o-trifluoromethyl-phenyl)-1H-1,2,4-triazole.

Other representative compounds of formula I are:
3-(2-Chloro-4-nitrophenyl)-1-methyl-5-(o-trifluoromethyl-phenyl)-1H-1,2,4-triazole, 3-(2-chloro-3-pyridyl)-1-methyl-5-(o-trifluoromethyl-phenyl)-1H-1,2,4-triazole, 3-(o-methylthiophenyl)-1-methyl-5-(o-trifluoromethyl-phenyl)-1H-1,2,4-triazole, 3-(2-chloro-4-trifluoromethyl-phenyl)-1-methyl-5-(o-trifluoromethyl-phenyl)-1H-1,2,4-triazole, 1-methyl-3-(2,3,6-trichlorophenyl)-5-(o-trifluoromethyl-phenyl)-1H-1,2,4-triazole, 1-methyl-3-(p-nitrophenyl)-5-(o-trifluoromethyl-phenyl)-1H-1,2,4-triazole, 1-methyl-3-(o-nitrophenyl)-5-(o-trifluoromethyl-phenyl)-1H-1,2,4-triazole.

3-(2-chloro-4-pyridyl)-1-methyl-5-(o-trifluoromethyl-phenyl)-1H-1,2,4-triazole, 3-(4-chloro-3-pyridyl)-1-methyl-5-(o-trifluoromethyl-phenyl)-1H-1,2,4-triazole, 1-methyl-3-(2,4,6-trifluorophenyl)-5-(o-trifluoromethyl-phenyl)-1H-1,2,4-triazole, 1-methyl-3-pentafluorophenyl-5-(o-trifluoromethyl-phenyl)-1H-1,2,4-triazole.

3-(o-ethylphenyl)-1-methyl-5-(o-trifluoromethyl-phenyl)-1H-1,2,4-triazole, 3-(2-chloro-6-methylphenyl)-1-methyl-5-(o-trifluoromethyl-phenyl)-1H-1,2,4-triazole, 3-(o,p-dimethylphenyl)-1-methyl-5-(o-trifluoromethyl-phenyl)-1H-1,2,4-triazole, 3-(2-chloro-4-methylphenyl)-1-methyl-5-(o-trifluoromethyl-phenyl)-1H-1,2,4-triazole, 3-(4-chloro-2-methylphenyl)-1-methyl-5-(o-trifluoromethyl-phenyl)-1H-1,2,4-triazole, 3-(o-trifluoromethoxy-phenyl)-1-methyl-5-(o-trifluoromethyl-phenyl)-1H-1,2,4-triazole, 3-(o-difluoromethyl-phenyl)-1-methyl-5-(o-trifluoromethyl-phenyl)-1H-1,2,4-triazole, 3-(o-chlorodifluoromethyl-phenyl)-1-methyl-5-(o-trifluoromethyl-phenyl)-1H-1,2,4-triazole, 3-(o-dichloromethyl-phenyl)-1-methyl-5-(o-trifluoromethyl-phenyl)-1H-1,2,4-triazole, 1-chloromethyl-3-(o-chlorophenyl)-5-(o-trifluoromethyl-phenyl)-1H-1,2,4-triazole, 3-(o-chlorophenyl)-5-(o-trifluoromethyl-phenyl)-1-vinyl-1H-1,2,4-triazole, 3-(o,o'-difluorophenyl)-1-methyl-5-(4-trifluoromethyl-3-pyridyl)-1H-1,2,4-triazole and 3-(2-chloro-4-fluorophenyl)-1-methyl-5-(4-trifluoromethyl-3-pyridyl)-1H-1,2,4-triazole.

The compounds of this invention are prepared by the processes described below.

(a) Reacting a 1H- or 2H-1,2,4-triazole of the general formula

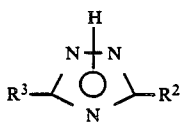

II wherein $R^2$ and $R^3$ are as defined above, with a compound of the general formula $R^1$—X  III wherein
$R^1$ is as defined above,
and X is a leaving group such as halogen (especially chlorine, bromine or iodine), mesyloxy or tosyloxy.

The reaction according to procedure (a) is conveniently carried out in an inert diluent as well as in the presence of a base. Especially suitable as diluents are inert organic solvents such as lower alkanols, e.g. methanol or ethanol, aliphatic or cyclic ethers, e.g. diethyl ether or tetrahydrofuran, and dipolar aprotic solvents, e.g. dimethylformamide. An alkali alcoholate, e.g. sodium methylate or sodium ethylate, or sodium hydride is preferably used as the base. In carrying out this procedure the reaction temperatures can be varied in a wide range, whereby in general the reaction is carried out at temperatures between $-20°$ C. and $70°$ C. or preferably between $0°$ C. and $30°$ C.

(b) Reacting a compound of the general formula

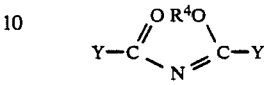

IV wherein one of the symbols Y stands for $R^2$ and the other stands for $R^3$, whereby $R^2$ and $R^3$ are as defined above, and $R^4$ is a lower alkyl residue, or an acid addition salt thereof with a hydrazine of the general formula $R^1$—NH—NH$_2$  V wherein $R^1$ is as defined above.

The reaction according to procedure (b) is conveniently carried out in an inert diluent, especially a chlorinated hydrocarbon, e.g. methylene chloride or carbon tetrachloride, an aliphatic or cyclic ether, e.g. tetrahydrofuran, or an aliphatic nitrile, e.g. acetonitrile. In carrying out this procedure the reaction temperatures can also be varied in a wide range, whereby the reaction is preferably carried out at temperatures between $10°$ C. and $50°$ C.

(c) For the preparation of those compounds of formula I in which $R^1$ is $C_{1-4}$-alkyl or $C_{2-4}$-alkenyl, reacting an imidic ester of the general formula

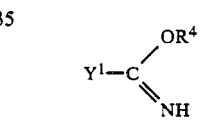

VI wherein $Y^1$ stands for $R^2$ or for $R^3$ and $R^4$ and $R^2$ or $R^3$ are as defined above, or an acid addition salt thereof with an acid hydrazide of the general formula

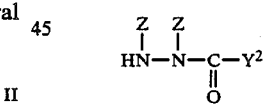

VII wherein one of the symbols Z is hydrogen and the other is $C_{1-4}$-alkyl or $C_{2-4}$-alkenyl, and $Y^2$ stands for $R^2$ (when $Y^1$ in formula VI is $R^3$) or for $R^3$ (when $Y^1$ in formula VI is $R^2$), whereby $R^2$ or $R^3$ as defined above, to an acylamidrazone and cyclizing this by heating.

The reaction according to procedure (c) can be carried out with or without the use of an inert diluent depending on the reactants. Where one or both of the reactants cannot be melted without decomposition, the reaction is conveniently carried out in an inert organic solvent such as an aliphatic alcohol, e.g. methanol; an aromatic, e.g. toluene or a xylene; a halogenated aromatic hydrocarbon, e.g. chlorobenzene; or dimethylformamide. The reaction mixture is held at an elevated temperature, advantageously in the temperature range of about $80°$ C. to about $150°$ C. When a diluent is used, the reaction mixture is suitably initially heated to its reflux temperature and after evaporation of the diluent the heating is continued, optionally at higher temperatures, e.g. up to about 200° C., in order to expedite the cyclization of the acylamidrazone of the general formula

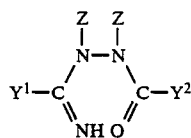

wherein $Y^1$, $Y^2$ and the symbols Z are as defined above, which is formed as the intermediate. For the same purpose and independently of the presence or absence of a diluent there can be used an acidic catalyst such as a mineral acid, e.g. hydrochloric acid or hydrobromic acid, or an aromatic sulphonic acid, e.g. p-toluenesulphonic acid, or an acid addition salt, e.g. the hydrochloride of the imidic ester of formula VI.

(d) For the preparation of those compounds of formula I in which $R^1$ is $C_{1-4}$-alkyl or $C_{2-4}$-alkenyl, reacting a diacyl-, monothiodiacyl- or dithiodiacylamine of the general formula

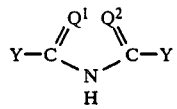

wherein the symbols Y are as defined above, and $Q^1$ and $Q^2$ each individually are oxygen or sulphur, with a hydrazine of the general formula

wherein $R^{1'}$ is $C_{1-4}$-alkyl or $C_{2-4}$-alkenyl.

Procedure (d) is an Einhorn-Brunner reaction; this is conveniently carried out using a diluent, especially an organic solvent such as an alcohol, e.g. ethanol, an aliphatic or cyclic ether, e.g. dioxan, a chlorinated aromatic, e.g. chlorobenzene, or acetic acid at elevated temperature, preferably at temperatures between about 50° C. and the reflux temperature of the reaction mixture.

(e) For the preparation of those compounds of formula I in which $R^1$ is $C_{1-4}$-haloalkyl, treating a 1- or 2-hydroxyalkyl-1H- or 2H-1,2,4-triazole of the general formula

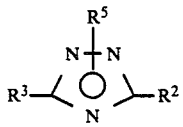

wherein $R^5$ is $C_{1-4}$-hydroxyalkyl and $R^2$ and $R^3$ are as defined above, with a halogenating agent.

The halogenation in accordance with procedure (e) can be carried out in general according to methods which are familiar to a person skilled in the art. For example, phosphorus pentachloride, trionyl chloride or phosphorus oxychloride is used as the chlorinating agent or phosphorus tribromide is used as the brominating agent. The halogenation is conveniently carried out in the presence of an inert diluent, especially an aprotic organic solvent, and optionally also in the presence of a base. To the preferred diluents there belong aliphatic and aromatic hydrocarbons such as n-hexane, benzene, toluene and xylenes; halogenated aliphatic hydrocarbons such as methylene chloride, chloroform and carbon tetrachloride; halogenated aromatic hydrocarbons such as chlorobenzene; and tertiary amines such as triethylamine and pyridine. Triethylamine, pyridine and calcium carbonate are preferred basis. The reaction temperatures lie in general between 0° C. and the reflux temperature of the reaction mixture, preferably between room temperature and the reflux temperature. The halogenating agent is preferably used in excess.

In the case of the manufacture of the acid addition salts of the compounds of formula I, the compound of formula I are reacted with the desired acids in conventional manner, for example by dissolution of the compound of formula I in a suitable solvent, such as diethyl ether, ethanol, ethyl acetate, toluol or methylene chloride, and addition of the acid, such as hydrogen chloride in the form of concentrated hydrochloric acid or gaseous hydrogen chloride. The resulting precipitate of the acid addition salt can then be isolated, e.g. by filtration.

As formula II, the starting material in procedure (a), embraces the compounds of the general formulae

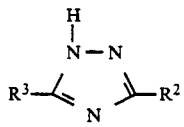

and

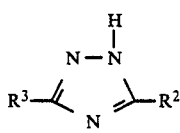

the product of formula I in this procedure is normally obtained as a mixture of the compounds of the correspondig formulae Ia and Ib. The individual compounds of formulae Ia and Ib can be isolated from the mixture according to separation methods known per se, e.g. by column chromatography.

In the case of procedures (b) and (c) there is to be understood under "lower alkyl residue" ($R^4$) especially an alkyl residue containing 1 to 6 carbon atoms, but preferably methyl or ethyl. Examples of acid addition salts of the compounds of formula IV or VI are hydrochlorides and hydrobromides.

The isolation and the purification of the thus-manufactured compounds of formula I can be carried out using standard procedures well known to the art. For example, the compound of formula I can be isolated in the form of an acid addition salt thereof and this salt then treated with aqueous sodium hydroxide to isolate the free 1,2,4-triazole, which itself is purified by recrystallization, distillation or column chromatography.

The 1H- and 2H-1,2,4-triazoles of formula II which are used as starting materials in procedure (a) are novel and can be produced, for example, from azines of the general formula

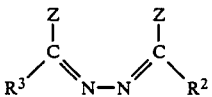

wherein Z is a leaving group such as halogen, preferably chlorine, and $R^2$ and $R^3$ are as defined above, namely (i) by reaction with ammonia, conveniently in an organic solvent such as a lower alkanol, e.g. ethanol, an aliphatic or cyclic ether such as tetrahydrofuran, or an aromatic, e.g. toluene, at elevated temperature such as in the temperature range of 30° C. to 100° C., but preferably at the reflux temperature of the reaction mixture, or (ii) by reaction with hydrazine and subsequent acid treatment and reductive deamination. The reaction with hydrazine is conveniently carried out in an inert diluent such as a diluent specified in connection with (i) (reaction with ammonia) at an elevated temperature such as in the temperature range of 20° C. to 100° C., preferably 40° C. to 80° C. The subsequent acid treatment is conveniently carried out using a strong mineral acid such as concentrated hydrochloric acid with heating, whereafter the mixture is made neutral. The 4-amino-1,2,4-triazole of the general formula

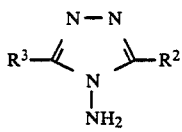  XII which is formed as an intermediate is then conveniently desaminated with nitrous acid, whereby this acid is suitably generated in situ from an alkali metal nitrite such as sodium nitrite in the presence of an acid such as acetic acid. The deamination is carried out at low temperatures, especially between 0° C. and 20° C.

The azines of formula XI can be produced in turn from the corresponding diacylhydrazines of the general formula

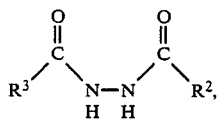  XIII e.g. by chlorination with phosphorus pentachloride at an elevated temperature, conveniently in a chlorinated aromatic, as is described, for example, in Liebigs Annalen der Chemie 749, 5 and 11 (1971).

Moreover, the 1H- and 2-H-1,2,4-triazoles of formula II can be produced analogously to procedures (b), (c) and (d), whereby in place of the hydrazine of formula V there is used an unsubstituted hydrazine or in place of the acid hydrazide of formula VII there is used an acid hydrazide of the formula

  XIV wherein $Y^2$ is as defined above.

The starting materials of formulae III and V or V' are either known or can be produced according to methods known per se. Likewise, the compounds of formula IV used as starting materials in procedure (b) are for the most part known; these can be produced, in particular, in a manner known per se by acylating an imidic ester of formula VI with an acylating agent containing the group of the formula YCO-, such as the corresponding acid chloride, bromide or anhydride, in the presence of an organic or inorganic acid acceptor, e.g. sodium carbonate, triethylamine or pyridine.

The imidic esters of formula VI and their acid addition salts which are used as starting materials in procedure (c) and for the production of the compounds of formula IV are either known or can be produced in a manner known per se, for example by treating a nitrile $Y^1CN$ with an anhydrous alcohol $R^4OH$ in the presence of an acidic catalyst such as hydrogen chloride (Pinner reaction) or by O-alkylating an amide $Y^1CONH_2$ with an alkylating agent containing the residue $R^4$, such as a Meerwein salt, e.g. triethyloxonium tetrafluoroborate, as is described in J. Org. Chem. 33, 1679-1680 (1968). The acid addition salts of the imidic esters VI produced in this manner can be converted into the corresponding free bases by conventional treatment with bases.

The acid hydrazides of formula VII which are used as starting materials in procedure (c) as well as the acid hydrazides of formula XIV are either known or can be produced according to methods known per se, for example by acylating hydrazine or $C_{1-4}$-monoalkylhydrazines with carboxylic acid esters or anhydrides containing the group of the formula YCO—, as is described, inter alia, in J.A.C.S. 80, 1895-1900 (1958) and J. Chem. Soc. (B) 1969, 1185-1191.

The diacylamines, monothiodiacylamines or dithiodiacylamines of formula VIII which are used as starting materials in procedure (d) are also known or can be produced according to methods known per se, for example by acylating amides of thioamides $Y^1$—$CQ^1NH_2$ with acyl halides or thioacyl halides $Y^2$—$CQ^2$—Hal, wherein $Y^1$, $Y^2$, $Q^1$ and $Q^2$ have the significances given above and Hal signifies halogen, especially chlorine or bromine. Such production methods are described, inter alia, in Rocz. Chem. 48, 243 (1974), J. Het. Chem. 19, 613 (1982), J. Het. Chem. 20, 1693-1695 (1983) and U.S. Pat. No. 4,414,221.

The 1- and 2-hydroxyalkyl-1H- or 2H-1,2,4-triazoles of formula IX which are used as starting materials in procedure (e) are novel; they can be produced, for example, analogously to procedure (a) or (b) when a compound of the formula $R^5$—X or $R^5$—NH—$NH_2$, wherein $R^5$ is $C_{1-4}$-hydroxyalkyl, is used therein in place of the compound of formula III or V, respectively.

The isolation and the purification of the thus-produced starting materials can be carried out using standard procedures well known in the art.

The compounds in accordance with the invention, i.e. the compounds of formula I and their acid addition salts are useful as pesticides. They have been shown to be especially valuable for the control of insects and mites, especially of Homoptera (especially aphids) such as e.g. *Aphis fabae, Aphis gossypii, Aphis pomi; Acyrthosiphon pisum, Acyrthosiphon dirhodum; Brevicoryne brassicae; Dyasphis devecta, Dysaphis pyri, Dysaphis plantaginea; Macrosiphum rosae, Macrosiphum avenae; Myzus persicae, Myzus cerasi; Phorodon humuli; Rhopalosiphum insertum, Rhopalosiphum padi; Toxoptera aurantii; Nasonovia ribisnigri; Hyalopterus pruni;* white flies such as e.g. *Trialeurodes vaporariorum; Aleurothrixus floccosus; Bemisia tabaci; Aleurodes proletella; Aleurocanthus woglumi; Dialeurodes citri;* aphids such as e.g. *Psylla mali, Psylla piri, Psylla pirisuga, Psylla piricula; Trioza apicalis;* mites which are of importance in plant protection such as e.g. Tetranychidae (spider mites), especially *Tetranychus urticae, Tetranychus cinnabarinus, Tetranychus turkestani, Tetranychus McDanieli, Tetranychus kanzawai; Panonychus ulmi, Panonychus citri; Phyllocoptruta oleivora; Aculus schlechtendali; Phyllocoptes vitis; Aceria essigi, Aceria gracilis; Cedidophyopsis ribis;*

*Eriophyes vitis; Eotetranychus sexmaculatus, Eotetranychus carpini; Hemitarsonemus latus;* mites which are of importance in veterinary medicine such as e.g. *Macronyssus bursa, Macronyssus sylviarum, Macronyssus lacoti; Dermanyssus gallinae;* ticks, especially of the families Ixodidae and Argasidae and of the orders Boophilus, Amblyomma, Hyalomma Rhipicephalus, Ixodes, Argas and Ornithodorus.

The compounds of this invention act as contact and feed poisons. Moreover, some of the compounds are taken up by various plants, so that the pests to be controlled are killed when they eat the plants. The compounds thus exhibit systemic activity.

The pest control composition in accordance with the invention contains an effective amount of at least one compound of general formula I, as defined above, or an acid addition salt of such a compound, as well as formulation adjuvants. The composition conveniently contains at least one of the following formulation adjuvants:

Solid carrier substances; solvents or dispersion media; tensides (wetting and emulsifying agents); dispersing agents (without tenside action); and stabilizers. With the use of these and other adjuvants the compounds of formula I, namely the pesticidally active substances, can be converted into the usual formulations such as solutions, suspensions, emulsions, emulsifiable concentrates, pastes, foams, dusts, powders and granulates.

As solid carrier substances there essentially come into consideration: natural mineral substances such as kaolin, aluminas, siliceous earth, talc, bentonite, chalk, limestone, quartz, dolomite, attapulgite, montmorillonite and diatomaceous earth; synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as dusts, powders or granulates.

As solvents or dispersion media there essentially come into consideration: aromatics such as toluene, xylenes, benzene and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol as well as their ethers and esters; ketones such as acetone, methyl ether ketone, methyl isobutyl ketone and cyclohexanone; and stongly polar solvents such as dimethylformamide N-methylpyrrolidone and dimethyl sulphoxide, such solvents or dispersion media preferably having flash points of at least 30° C. and boiling points of at least 50° C., and water. Among the solvents or dispersion media there also come into consideration so-called liquified gaseous extenders or carrier substances, these being products which are gaseous at room temperature and under normal pressure. Examples of such products are especially aerosol propellants such as halogenated hydrocarbons, e.g. dichlorodifluoromethane. When water is used as the solvent, organic solvents can e.g. also be used as auxiliary solvents.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzene sulphonates, e.g. calcium dodecylbenzenesulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration: lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminotetraacetic acid and polyglycols.

The pest control compositions in accordance with the invention can contain, in addition to the active substances of formula I, other active substances, e.g. other pest control agents, pest baits, fungicides, bactericides, plant growth regulators and fertilizers. Such combination compositions are suitable for intensifying the activity or for broadening the spectrum of activity. If desired, insufficiencies of hitherto known added agents can thereby also be compensated for.

It has been found that the compounds in accordance with the invention, especially those indicated hereinbefore as being especially preferred, can be used with advantage in combination with other acaricides, primarily with acaricides which are suitable for the control of mobile stages of mites. Examples of such acaricides are amitraz, avermectin, benzoximate, bromopropylate, chlorobenzilate, cyhexatin, dicofol, fenbutatin oxide, methidathion, propargite and ethyl 5,7-dihydro-6H-dibenz[c,e]azepine-6-carboximidate as well as pyrethroids having acaricidal activity such as, for example fluvalinate, biphenthrin and cyano-3-phenoxybenzyl-3-(2-chloro-2,3,3-trifluoroprop-1-enyl)-2,2-dimethylcyclopropanecarboxylate. The use can be carried out simultaneously as a mixture or separately. Thereby, the active substances in accordance with the invention can compensate for the disadvantage of the known acaricides having a main focus of activity against adult pests, in that the eggs and larvae which survive after the use of the known acaricides and which can develop rapidly into a new pest population are also killed.

The pest control compositions in accordance with the invention generally contain between 0.005 and 95 weight percent of the compound or compounds of this invention as the active substance. They can be present in a form which is suitable for storage and transport. In such forms, e.g. emulsifiable concentrates, the active substance concentration is normally in the higher region of the above concentration range. These forms can be diluted with the same or different formulation adjuvants to give active substance concentrations which are suitable for practical use and such concentrations normally lie in the lower region of the above concentration range. Emulsifiable concentrates generally contain 5 to 90 weight percent, preferably 10 to 80 weight percent, of the compound or compounds of this invention. As forms of use there come into consideration, inter alia, ready-for-use solutions, emulsions, suspensions, foams, powders, pastes, dusting compositions and granulates. The active substance concentrations in such ready-for-use compositions can be varied in wide limits. In spray liquors there can be present e.g. concentrations between 0.005 and 0.5 weight percent. In the Ultra-Low-Volume process there can be formulated spray liquors in which the active substance concentration is preferably from 10 to 20 weight percent, while the spray liquors formulated in the Low-Volume process and in the High-Volume process preferably have an active substance concentration of 0.01 to 0.5 and 0.005 to 0.1 weight percent, respectively. Granulates preferably contain from 5 to 50 weight percent of the compound or compounds of this invention as the active substance(s).

The pest control compositions in accordance with the invention can be manufactured by mixing at least one compound of general formula I or an acid addition salt thereof with formulation adjuvants.

The manufacture of the compositions can be carried out in a known manner, e.g. by mixing the active substance with solid carrier substances, by dissolution or suspension in suitable solvents or dispersion media, if necessary using tensides as wetting or emulsifing agents, or dispersing agents, by diluting pre-prepared emulsifiable concentrates with solvents or dispersion media etc.

In the case of pulverous compositions the active substance can be mixed with a solid carrier substance, e.g. by grinding together; or the solid carrier substance can be impregnated with a solution or suspension of the active substance and then the solvent or suspension medium can be removed by evaporation, by heating or by sucking-off under reduced pressure. By adding tensides or dispersing agents such pulverous compositions can be made readily wettable with water, so that they can be converted into aqueous suspensions which are suitable e.g. as spray compositions.

The compounds of formula I or their acid addition salts can also be mixed with a tenside and a solid carrier substance to form a wettable powder which is dispersible in water or they can be mixed with a solid granulated carrier substance to form a granulate.

If desired, the compound of formula I or an acid addition salt thereof can be dissolved in a water-immiscible solvent such as, for example, an alicyclic ketone, which conveniently contains a dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable cooncentrates or ready-for-use emulsions.

The method in accordance with the invention for the control of pests comprises treating the locus to be protected or the pests themselves with an effective amount of a compound in accordance with the invention or of a pest control composition in accordance with the invention. This method of use can be carried out by application to the soil or leaves or by application to the animals, supplies or materials to be protected, depending on the kind of pests to be controlled. The control is achieved, for example, by contact or by intake with the feed.

The use can be carried out in a conventional manner, e.g. by sprinkling, spraying, atomising, dusting, scattering, drilling-in, smoking, watering, steeping or coating. Pulverous preparations can be applied to the pests or to the locus to be protected, e.g. plants or animals, as e.g. dusting agents with the aid of the usual dusting appliances. Aqueous suspensions can be used e.g. as spray compositions.

When used in plant protection a dosage of about 120–500 g of active substance [compound(s) of formula I]/ha, is usually sufficient, e.g. as in the case of the application of 200 l of a spray liquor which contains 0.006–0.025 weight percent of active substance to 1 ha of cultivated land.

The following Examples serve to illustrate the invention in more detail.

I. Preparation of the active substances of formula I:

EXAMPLE 1

0.19 g of sodium hydride is placed in 10 ml of N,N-dimethylformamide. A solution of 2.3 g of 3-(o-fluorophenyl)-5-(o-trifluoromethyl-phenyl)-1H-1,2,4-triazole in 15 ml of N,N-dimethylformamide is allowed to drop in while stirring during 10 minutes. After stirring for a further 45 minutes the solution, which has meanwhile become brown, is treated dropwise with 1.17 g of methyl iodide while cooling with ice. The reaction mixture is stirred for a further one hour and thereafter poured on to ice-water, and the aqueous mixture is extracted three times with ethyl acetate. The combined extracts are washed with water and saturated sodium chloride solution, dried over anhydrous sodium sulphate and evaporated under reduced pressure. In this manner there is obtained a mixture of isomeric N-methyltriazoles which can be separated by chromatography on silica gel. By elution with n-hexane/ethyl acetate (19:1) there is obtained pure 5-(o-fluorophenyl)-1-methyl-3-(o-trifluoromethyl-phenyl)-1H-1,2,4-triazole as a resinous product, $^1$H-NMR(CDCl$_3$): 3.93 (d, C$\underline{H}_3$, coupling with F).

Further elution with n-hexane/ethyl acetate (9:1) gives pure 3-(o-fluorophenyl)-1-methyl-5-(o-trifluoromethyl-phenyl)-1H-1,2,4-triazole, m.p. 104°–107° C., $^1$H-NMR(CDCl$_3$): 3.82 (s, C$\underline{H}_3$).

In an analogous manner, starting from 3-(o-chlorophenyl)-5-(o-trifluoromethyl-phenyl)-1H-1,2,4-triazole and methyl iodide there is obtained a mixture of isomeric N-methyltriazoles and therefrom there are obtained pure 5-(o-chlorophenyl)-1-methyl-3-(o-trifluoromethyl-phenyl)-1H-1,2,4-triazole as a resinous product, $^1$H-NMR(CDCl$_3$): 3.86 (s, C$\underline{H}_3$); and pure 3-(o-chlorophenyl)-1-methyl-5-(o-trifluoromethyl-phenyl)-1H-1,2,4-triazole, m.p. 90°–92° C., $^1$H-NMR(CDCl$_3$): 3.78 (s, C$\underline{H}_3$);

starting from 3-(o-chlorophenyl)-5-(o-trifluoromethyl-phenyl)-1H-1,2,4-triazole and ethyl bromide there is obtained a mixture of isomeric N-ethyltriazoles and therefrom there are obtained pure 1-ethyl-5-(o-chlorophenyl)-3-(o-trifluoromethyl-phenyl)-1H-1,2,4-triazole as a resinous product, $^1$H-NMR(CDCl$_3$): 1.47 (t, CH$_2$CH$_3$), 4.10 (q, CH$_2$CH$_3$); and pure 1-ethyl-3-(o-chlorophenyl)-5-(o-trifluoromethyl-phenyl)-1H-1,2,4-triazole, likewise as a resinous product, $^1$H-NMR(CDCl$_3$): 1.45 (t, CH$_2$CH$_3$), 4.04 (q, CH$_2$CH$_3$);

starting from 3-(o-chlorophenyl)-5-(o-trifluoromethyl-phenyl)-1H-1,2,4-triazole and allyl bromide there is obtained a 1:1 mixture of 1-allyl-5-(o-chlorophenyl)-3-(o-trifluoromethyl-phenyl)-1H-1,2,4-triazole and 1-allyl-3-(o-chlorophenyl)-5-(o-trifluoromethyl-phenyl)-1H-1,2,4-triazole as an oil, $^1$H-NMR(CDCl$_3$): 4.63 and 4.71 (m, CH$_2$CH=CH$_2$), 5.09 and 5.22 (m, CH$_2$CH=CH$_2$), 5.91–6.01 (m, CH$_2$CH=CH$_2$); as well as the corresponding 1-propenyltriazoles, namely a 1:1 mixture of 5-(o-chlorophenyl)-1-(1-propenyl)-3-(o-trifluoromethyl-phenyl)-1H-1,2,4-triazole and 3-(o-chlorophenyl)-1-(1-propenyl)-5-(o-trifluoromethyl-phenyl)-1H-1,2,4-triazole, these being additionally present as a E/Z mixture; $^1$H-NMR(CDCl$_3$): 1.77, 1.81, 2.0 and 2.10 (in each case dd, CH$_3$CH=CH);

starting from 3-(o-chlorophenyl)-5-(o-trifluoromethyl-phenyl)-1H-1,2,4-triazole and n-propyl iodide there is obtained a 11:9 mixture of 5-(o-chloro-phenyl)-1-(n-propyl)-3-(o-trifluoromethyl-phenyl)-1H-1,2,4-triazole and 3-(o-chlorophenyl)-1-(n-propyl)-5-(o-trifluoromethyl-phenyl)-1H-1,2,4-triazole as an oil, $^1$H-NMR(CDCl$_3$): 0.84 and 0.89 (t, CH$_3$CH$_2$), 1.85–1.96 (m, CH$_3$CH$_2$CH$_2$), 4.02 and 3.94 (t, CH$_3$CH$_2$CH$_2$N);

starting from 3-(o-chlorophenyl)-5-(o-trifluoromethyl-phenyl)-1H-1,2,4-triazole and isopropyl iodide there is obtained a 11:9 mixture of 5-(o-chloro-phenyl)-1-isopropyl-3-(o-trifluoromethyl-phenyl)-1H-1,2,4-triazole and 3-(o-chlorophenyl)-1-isopropyl-5-(o-trifluoromethyl-phenyl)-1H-1,2,4-triazole as a solid, m.p. 82°–85° C.;

starting from 3,5-di(o-trifluoromethyl-phenyl)-1H-1,2,4-triazole and methyl iodide there is obtained 1-methyl-3,5-di(o-trifluoromethyl-phenyl)-1H-1,2,4-triazole, m.p. 108°–111° C.;

starting from 3-(o-tolyl)-5-(o-trifluoromethyl-phenyl)-1H-1,2,4-triazole and methyl iodide there is obtained a 1:1 mixture of 1-methyl-3-(o-tolyl)-5-(o-trifluoromethyl-phenyl)-1H-1,2,4-triazole and 1-methyl-5-(o-tolyl)-3-(o-trifluoromethyl-phenyl)-1H-1,2,4-triazole as an oil, $^1$H-NMR(CDCl$_3$): 2.3 and 2.63 (s, C—CH$_3$), 3.76 and 3.85 (s, N—CH$_3$), 7.2–8.2 (8 aromatic H);

starting from 3-(o-fluorophenyl)-5-(o-trifluoromethyl-phenyl)-1H-1,2,4-triazole and ethyl bromide there is obtained a mixture of isomeric N-ethyltriazoles and therefrom there are obtained pure 1-ethyl-3-(o-fluorophenyl)-5-(o-trifluoromethyl-phenyl)-1H-1,2,4-triazole, m.p. 72°–74° C.; and pure 1-ethyl-5-(o-fluorophenyl)-3-(o-trifluoromethyl-phenyl)-1H-1,2,4-triazole, $^1$H-NMR(CDCl$_3$): 1.51 (t, CH$_3$), 4.23 (q, CH$_2$), 7.05–8.1 (8 aromatic H);

starting from 3-(o,o'-dichlorophenyl)-5-(o-trifluoromethyl-phenyl)-1H-1,2,4-triazole and methyl iodide there is obtained a mixture of isomeric N-methyltriazoles and therefore there are obtained pure 5-(o,o'-dichlorophenyl)-1-methyl-3-(o-trifluoromethyl-phenyl)-1H-1,2,4-triazole, m.p. 101°–103° C.; and pure 3-(o,o'-dichlorophenyl)-1-methyl-5-(o-trifluoromethyl-phenyl)-1H-1,2,4-triazole as a resinous product, mass spectrum: 371 (55), 352 (2), 200 (100), 181 (12), 152 (55).

EXAMPLE 2

A solution of 2 g of ethyl o,o'-difluorobenzimidate in 15 ml of diethyl ether is treated with 1.09 g of triethylamine and cooled to 0°–5° C. by means of an ice-bath. 2.25 g of o-trifluoromethyl-benzoyl chloride in 5 ml of diethyl ether are then added dropwise thereto during 10 minutes and the reaction mixture is stirred at 0°–5° C. for a further one hour. For the working-up, the mixture is poured on to ice-water and the aqueous mixture is extracted three times with diethyl ether. The combined extracts are washed in sequence with water, semi-saturated sodium chloride solution and saturated sodium chloride solution, dried over anhydrous sodium sulphate and evaporated under reduced pressure. In this manner there is obtained crude ethyl N-(o-trifluoromethyl-benzyl)-o,o'-difluorobenzimidate (4.94 g) as a moist yellow solid, m.p. 64°–69° C.

Without further purification 4.0 g of the above crude product are placed in methylene chloride and cooled to 10° C. 0.54 g of methylhydrazine is allowed to drop in within 3 minutes while stirring, the mixture is stirred at room temperature for a further 30 minutes and then heated to reflux temperature for 30 minutes. A further 0.54 g of methylhydrazine is subsequently added and the mixture is again heated to reflux temperature for 30 minutes in order to allow the remaining starting material to react. The mixture is poured into water and extracted twice with methylene chloride, the combined extracts are washed with water, dried over anhydrous sodium sulphate and evaporated under reduced pressure. The oily residue is purified by chromatography on silica gel with n-hexane/ethyl acetate (4:1). In this manner there is obtained 3-(o,o'-difluorophenyl)-1-methyl-5-(o-trifluoromethyl-phenyl)-1H-1,2,4-triazole as a solid, m.p. 103°–107° C.

In an analogous manner, starting from ethyl o-bromobenzimidate and o-trifluoromethyl-benzoyl chloride there is obtained crude ethyl N-(o-trifluoromethyl-benzoyl)-o-bromobenzimidate and therefrom with methylhydrazine there is obtained 3-(o-bromophenyl)-1-methyl-5-(o-trifluoromethyl-phenyl)-1H-1,2,4-triazole, m.p. 90°–94° C.;

starting from ethyl o,p-dichlorobenzimidate and o-trifluoromethyl-benzoyl chloride there is obtained ethyl (o-trifluoromethyl-benzoyl)-o,p-dichlorobenzimidate and therefrom with methylhydrazine there is obtained 3-(o,p-dichlorophenyl)-1-methyl-5-(o-trifluoromethyl-phenyl)-1H-1,2,4-triazole, m.p. 101°–103° C., $^1$H-NMR(CDCl$_3$): 3.80 (s, CH$_3$), 7.2–8.05 (7 aromatic H);

starting from ethyl o-methoxybenzimidate and o-trifluoromethyl-benzoyl chloride there is obtained ethyl N-(o-trifluoromethyl-benzoyl)-o-methoxybenzimidate and therefrom with methylhydrazine there is obtained 3-(o-anisyl)-1-methyl-5-(o-trifluoromethyl-phenyl)-1H-1,2,4-triazole, m.p. 74°–78° C.;

starting from ethyl 2,5-dichlorobenzimidate and o-trifluoromethyl-benzoyl chloride there is obtained ethyl N-(o-trifluoromethyl-benzoyl)-2,5-dichlorobenzimidate and therefrom with methylhydrazine there is obtained 3-(2,5-dichlorophenyl)-1-methyl-5-(o-trifluoromethyl-phenyl)-1H-1,2,4-triazole, m.p. 60°-63° C.;

starting from methyl nicotinimidate and o-trifluoromethyl-benzoyl chloride there is obtained methyl N-(o-trifluoromethyl-benzoyl)-3-pyridylcarboximidate and therefrom with methylhydrazine there is obtained 1-methyl-3-(3-pyridyl)-5-(o-trifluoromethyl-phenyl)-1H-1,2,4-triazole, $^1$H-NMR(CDCl$_3$): 3.76 (s, C$\underline{H}_3$), 7.3–8.0 (CH-4 and 4 aromatic H), 8.43 (ddd, C$\underline{H}$-5), 8.68 (dd, C$\underline{H}$-6), 9.41 (d, C$\underline{H}$-2);

starting from ethyl 2-chloro-6-fluorobenzimidate and o-trifluoromethyl-benzoyl chloride there is obtained ethyl N-(o-trifluoromethyl-benzoyl)-2-chloro-6-fluorobenzimidate and therefrom with methylhydrazine there is obtained 3-(2-chloro-6-fluorophenyl)-1-methyl-5-(o-trifluoromethyl-phenyl)-1H-1,2,4-triazole, m.p. 80°-84° C.;

starting from ethyl o-chlorobenzimidate and o-trifluoromethyl-benzoyl chloride there is obtained ethyl N-(o-trifluoromethyl-benzoyl)-o-chlorobenzimidate, m.p. 64°-65° C., and therefrom with 2,2,2-trifluoroethylhydrazine there is obtained 3-(o-chlorophenyl)-1-(2,2,2-trifluoroethyl)-5-(o-trifluoromethyl-phenyl)-1H-1,2,4-triazole, $^1$H-NMR(CDCl$_3$): 4.62 (q, C$\underline{H}_2$CF$_3$), 7.3–8.1 (8 aromatic H);

starting from ethyl 2-pyridylcarboximidate and o-trifluoromethyl-benzoyl chloride there is obtained ethyl N-(o-trifluoromethyl-benzoyl)-2-pyridylcarboximidate and therefrom with methylhydrazine there is obtained 1-methyl-3-(2-pyridyl)-5-(o-trifluoromethyl-phenyl)-1H-1,2,4-triazole, $^1$H-NMR(CDCl$_3$): 3.8 (s, C$\underline{H}_3$), 7.15–8.0 (6H), 8.2 (m, 1H), 8.73 (m, 1H);

starting from methyl isonicotinimidate and o-trifluoromethyl-benzoyl chloride there is obtained crude methyl N-(o-trifluoromethyl-benzoyl)-4-pyridylcarboximidate and therefrom with methylhydrazine there is obtained 1-methyl-3-(4-pyridyl)-5-(o-trifluoromethyl-phenyl)-1H-1,2,4-triazole, m.p. 143°-146° C.;

starting from ethyl 2-chloro-4-fluorobenzimidate and o-trifluoromethyl-benzoyl chloride there is obtained ethyl N-(o-trifluoromethyl-benzoyl)-2-chloro-4-fluorobenzimidate and therefrom with methylhydrazine there is obtained 3-(2-chloro-4-fluorophenyl)-1-methyl-5-(o-trifluoromethyl-phenyl)-1H-1,2,4-triazole, m.p. 67°-69° C.;

starting from ethyl o-iodobenzimidate and o-trifluoromethylbenzoyl chloride there is obtained crude ethyl N-(o-trifluoromethyl-benzoyl)-o-iodobenzimidate and therefrom with methylhydrazine there is obtained 3-(o-iodophenyl)-1-methyl-5-(o-trifluoromethyl-phenyl)-1H-1,2,4-triazole, m.p. 84°-88° C.;

starting from ethyl o,p-difluorobenzimidate and o-trifluoromethyl-benzoyl chloride there is obtained ethyl N-(o-trifluoromethyl-benzoyl)-o,p-difluorobenzimidate and therefrom with methylhydrazine there is obtained 3-(o,p-difluorophenyl)-1-methyl-5-(o-trifluoromethyl-phenyl)-1H-1,2,4-triazole, m.p. 54°-56° C.;

starting from ethyl 4-chloro-2-fluorobenzimidate and o-trifluoromethyl-benzoyl chloride there is obtained ethyl N-(o-trifluoromethyl-benzoyl)-2-fluoro-4-chlorobenzimidate and therefrom with methylhydrazine there is obtained 3-(4-chloro-2-fluorophenyl)-1-methyl-5-(o-trifluoromethyl-phenyl)-1H-1,2,4-triazole, m.p. 109.5°-112° C.;

starting from ethyl 3-chloro-2-fluorobenzimidate and o-trifluoromethyl-benzoyl chloride there is obtained ethyl N-(o-trifluoromethyl-benzoyl)-2-fluoro-3-chlorobenzimidate and therefrom with methylhydrazine there is obtained 3-(3-chloro-2-fluorophenyl)-1-methyl-5-(o-trifluoromethyl-phenyl)-1H-1,2,4-triazole, m.p. 137°-140° C.;

starting from ethyl o-trifluoromethyl-benzimidate and o,o'-difluorobenzoyl chloride there is obtained ethyl N-(o,o'-difluorobenzoyl)-o-trifluoromethyl-benzimidate and therefrom with methylhydrazine there is obtained 3-(o-trifluoromethyl-phenyl)-1-methyl-5-(o,o'-difluorophenyl)-1H-1,2,4-triazole, m.p. 81°-86° C.;

starting from ethyl o,o'-difluorobenzimidate and o-trifluoromethyl-benzoyl chloride there is obtained ethyl N-(otrifluoromethyl-benzoyl)-o,o'-difluorobenzimidate and therefrom with ethylhydrazine there is obtained 1-ethyl-3-(o,o'-difluorophenyl)-5-(o-trifluoromethyl-phenyl)-1H-1,2,4-triazole, m.p. 86°-89° C.;

starting from ethyl 2,3-dichlorobenzimidate and o-trifluoromethyl-benzoyl chloride there is obtained ethyl N-(o-trifluoromethyl-benzoyl)-2,3-dichlorobenzimidate and therefrom with methylhydrazine there is obtained 3-(2,3-dichlorophenyl)-1-methyl-5-(o-trifluoromethyl-phenyl)-1H-1,2,4-triazole, m.p. 86°-88° C.;

starting from ethyl o-chlorobenzimidate and 4-trifluoromethyl-nicotinoyl chloride there is obtained ethyl N-(4-trifluoromethyl-nicotinoyl)-2-chlorobenzimidate and therefrom with methylhydrazine there is obtained 3-(o-chlorophenyl)-1-methyl-5-(4-trifluoromethyl-3-pyridyl)-1H-1,2,4-triazole, $^1$H-NMR(CDCl$_3$): 3.85 (s, N-CH$_3$), 7.6–8.1 (5 aromatic H), 8.9–9.2 (2 aromatic H); mass spectrum: 338 (100), 319 (5), 166 (94), 138 (95);

starting from ethyl o-cyanobenzimidate and o-trifluoromethyl-benzoyl chloride there is obtained ethyl N-(o-trifluoromethyl-benzoyl)-o-cyanobenzimidate and therefrom with methylhydrazine there is obtained 3-(o-cyanophenyl)-1-methyl-5-(o-trifluoromethyl-phenyl)-1H-1,2,4-triazole, m.p. 96.5°-99° C.

EXAMPLE 3

A mixture of 1.1 g of 3-(o-chlorophenyl)-1-(2-hydroxyethyl)-5-(o-trifluoromethyl-phenyl)-1H-1,2,4-triazole, 1.09 g of thionyl chloride and 5 ml of toluene is heated at reflux temperature for 4 hours. The reaction mixture is then evaporated, the residue is taken up in diethyl ether, the soluton is washed twice with 5% sodium bicarbonate solution, dried over anhydrous magnesium sulphate and evaporated. In this manner there is obtained 1-(2-chloroethyl)-3-(o-chlorophenyl)-5-(o-trifluoromethyl-phenyl)-1H-1,2,4-triazole, m.p. 66°-68° C.

II. Production of the starting materials of formula II:

EXAMPLE 4

A solution of 2.01 g of hydrazine hydrate in 6 ml of ethanol is heated to reflux temperature. 3.63 g of the azine from o-fluorobenzoyl chloride and o-trifluoromethyl-benzoyl chloride dissolved in 30 ml of warm ethanol is allowed to drop in within 15 minutes and the mixture is reacted at reflux temperature for 45 minutes. The ethanol is then distilled off, the oily residue is treated with 25 ml of concentrated hydrochloric acid (at least 32%) within 10 minutes and the mixture is stirred at 80° C. for one hour. The mixture is then cooled by means of an ice-bath and made basic by the addition of 30 ml of ammonia solution (about 25%). Three-fold extraction with methylene chloride, two-fold washing with water, drying over anhydrous sodium sulphate and evaporation of the solvent gives 3.21 g of crude 4-amino-3-(o-fluorophenyl)-5-(o-trifluoromethyl-phenyl)-4H-1,2,4-triazole.

Without further purification the above crude product is dissolved in 42 ml of glacial acetic acid and a solution of 1.87 g of sodium nitrite in 8 ml of water is added dropwise to the solution at 15° C. within 15 minutes. The mixture is subsequently stirred for a further one hour and made weakly basic by the addition of 42 ml of ammonia solution. The precipitated product is filtered off under suction and dried at 70° C./200 mmHg. In this manner there is obtained pure 3-(o-fluorophenyl)-5-(o-trifluoromethyl-phenyl)-1H-1,2,4-triazole, m.p. 153°-155° C.

In an analogous manner,
starting from the azine from o-chlorobenzoyl chloride and o-trifluoromethyl-benzoyl chloride and hydrazine hydrate there is obtained 4-amino-3-(o-chlorophenyl)-5-(o-trifluoromethyl-phenyl)-4H-1,2,4-triazole and therefrom by deamination there is obtained 3-(o-chlorophenyl)-5-(o-trifluoromethyl-phenyl)-1H-1,2,4-trizole, m.p. 172°-175° C.;
starting from o-trifluoromethyl benzoyl azine dichloride and hydrazine hydrate there is obtained 4-amino-3,5-di(o-trifluoromethyl-phenyl)-4H-1,2,4-triazole and therefrom by deamination there is obtained 3,5-di(o-trifluoromethyl-phenyl)-1H-1,2,4-triazole, m.p. 189.5°-192° C.;
starting from the azine from o-toluyl chloride and o-trifluoromethyl-benzoyl chloride and hydrazine hydrate there is obtained 4-amino-3-(o-tolyl)-5-(o-trifluoromethyl-phenyl)-4H-1,2,4-triazole and therefrom by deamination there is obtained 3-(o-tolyl)-5-(o-trifluoromethyl-phenyl)-1H-1,2,4-triazole;
starting from the azine from o,o'-dichlorobenzoyl chloride and o-trifluoromethyl-benzoyl chloride and hydrazine hyxdrate there is obtained 4-amino-3-(o,o'-dichlorophenyl)-5-(o-trifluoromethyl-phenyl)-4H-1,2,4-triazole and therefrom by deamination there is obtained 3-(o,o'-dichloro-phenyl)-5-(o-trifluoromethyl-phenyl)-1H-1,2,4-triazole.

EXAMPLE 5

9.24 g of o-fluorobenzoyl hydrazide are added while stirring to a solution of 2.64 g of sodium hydroxide in 34 ml of water. The mixture is then cooled to 0°-5° C. and 13.76 g of o-trifluoromethyl-benzoyl chloride are allowed to drop in during 20 minutes. The reaction mixture is stirred at 5°-10° C. for a further one hour and subsequently diluted with 30 ml of water. The resulting crystal slurry is filtered off under suction, washed on the suction filter with a small amount of water and dried at 80° C./180 mmHg. In this manner there is obtained 1-(o-fluorobenzoyl)-2-(o-trifluoromethyl-benzoyl)-hydrazine, m.p. 171°-173° C.

17.4 g of the above product are added portionwise within 20 minutes to a solution, heated to 110° C., of 33.3 g of phosphorus pentachloride in 50 ml of 1,2-dichlorobenzene. The mixture is reacted at 110° C. for one hour and then the solvent and the excess phosphorus pentachloride are distilled off in a water-jet vacuum. The cooled residue is treated with water and extracted three times with ethyl acetate. The combined extracts are washed twice with water, dried over anhydrous sodium sulphate and evaporated under reduced pressure, and the solid residue is purified by chromatography on silica gel with n-hexane/ethyl acetate (19:1). In this manner there is obtained the pure azine from o-fluorobenzoyl chloride and o-trifluoromethyl-benzoyl chloride, m.p. 73°-75° C.

[With the subsequent use of n-hexane/ethyl acetate (2:1) as the elution agent there is obtained in smaller amount 2-(o-fluorophenyl)-5-(o-trifluoromethyl-phenyl)-1,3,4-oxadiazole, m.p. 68°-69° C. (after recrystallization from n-hexane/ethyl acetate), which results as a by-product.]

In an analogous manner,
starting from o-chlorobenzoyl hydrazide and o-trifluoromethyl-benzoyl chloride there is obtained 1-(o-chlorobenzoyl)-2-(o-trifluoromethyl-benzoyl)-hydrazine, m.p. 241°-243° C., and therefrom by chlorination there is obtained the azine from o-chlorobenzoyl chloride and o-trifluoromethyl-benzoyl chloride, m.p. 81.5°-82.5° C. (after recrystallization from isopropanol);
starting from o-trifluoromethylbenzoyl hydrazide and o-trifluoromethyl-benzoyl chloride there is obtained crude 1,2-di(o-trifluoromethyl-benzoyl)-hydrazine and therefrom by chlorination there is obtained o-trifluoromethyl-benzoyl azine dichloride m.p. 100°-104° C.;
starting from o-toluyl hydrazide and o-trifluoromethyl-benzoyl chloride there is obtained crude 1-(o-toluyl)-2-(o-trifluoromethyl-benzoyl)-hydrazine and therefrom by chlorination there is obtained and azine from o-toluyl chloride and o-trifluoromethyl-benzoyl chloride. m.p. 55°-57° C.;
starting from o,o'-dichlorobenzoyl hydrazide and o-trifluoromethyl-benzoyl chloride there is obtained 1-(o,o'-dichlorobenzoyl)-2-(o-trifluoromethyl-benzoyl)-hydrazine and therefrom by chlorination there is obtained the azine from o,o'-dichlorobenzoyl chloride and o-trifluoromethyl-benzoyl chloride.

III. Production of the starting materials of formula VI:

EXAMPLE 6

A solution of 39.2 g of triethyloxonium tetrafluoroborate in 325 ml of methylene chloride is treated with 32.5 g of o-trifluoromethyl-benzamide. After stirring at room temperature for 48 hours the reaction mixture is poured on to a mixture of 10% sodium carbonate solution and ice and the resulting mixture is extracted three times with methylene chloride. The combined extracts are then washed twice with 10% sodium carbonate solution, dried over anhydrous sodium sulphate and evaporated under reduced pressure. The oily, brown residue is distilled in a high vacuum. There is obtained pure ethyl o-trifluoromethyl-benzimidate, b.p. 67° C./0.15 mmHg.

In an analogous manner,
starting from 2,5-dichlorobenzamide and triethyloxonium tetrafluoromborate there is obtained ethyl 2,5-dichlorobenzimidate, m.p. 40°-43° C.;
starting from 4-chloro-2-fluorobenzamide and triethyloxonium tetrafluoroborate there is obtained ethyl 4-chloro-2-fluorobenzimidate as an oil; mass spectrum: 202 (3.5), 201 (1), 200 (10), 182 (2), 173 (27), 157 (100), 156 (75);
starting from o-iodobenzamide and triethyloxonium tetrafluoroborate there is obtained ethyl o-iodobenzimidate as an oil; $^1$H-NMR(CDCl$_3$): 1.42 (t, C$\underline{H}_3$), 4.38 (q, C$\underline{H}_2$), 6.8–7.6 (3 aromatic H+N$\underline{H}$), 7.8–8.05 (1 aromatic H);

starting from 3-chloro-2-fluorobenzamide and triethyloxonium tetrafluoroborate there is obtained ethyl 3-chloro-2-fluorobenzimidate as an oil; mass spectrum: 200 (10), 173 (25), 166 (15), 157 (100), 156 (73);

starting from o,p-difluorobenzamide and triethyloxonium tetrafluoroborate there is obtained ethyl o,p-difluorobenzimidate as an oil; mass spectrum: 184 (10), 166 (3), 157 (36), 141 (100), 140 (95);

starting from 2,3-dichlorobenzamide and triethyloxonium tetrafluoroborate there is obtained ethyl 2,3-dichlorobenzimidate as an oil; mass spectrum: 216 (16), 189 (20), 182 (9), 173 (100), 172 (56);

starting from 2-chloro-4-fluorobenzamide and triethyloxonium tetrafluoroborate there is obtained ethyl 2-chloro-4-fluorobenzimidate as an oil; $^1$H-NMR(CDCl$_3$): 1.43 (t, C$\underline{H}_3$), 4.40 (q, C$\underline{H}_2$), 6.9–7.8 (3 aromatic H+N$\underline{H}$).

IV. Preparation of the starting materials of formula IX:

EXAMPLE 7

Analogously to the procedure described in Example 2, starting from ethyl o-chlorobenzimidate and o-trifluoromethyl-benzoyl chloride there is obtained ethyl N-(o-trifluoromethyl-benzoyl)-o-chlorobenzimidate, m.p. 64°–65° C., and therefrom by means of 2-hydroxyethylhydrazine there is obtained 3-(o-chlorophenyl)-1-(2-hydroxyethyl)-5-(o-trifluoromethyl-phenyl)-1H-1,2,4-triazole, m.p. 115° C.

V. Formulation Examples:

EXAMPLE 8

An emulsifiable concentrate has the following composition:

|  | g/liter |
|---|---|
| Compound of formula I (active substance) | 250 |
| Nonylphenol-(10)ethoxylate (emulsifier) | 50 |
| Calcium dodecylbenzenesulphonate (emulsifier) | 25 |
| Mixture of mono-, di- and tri(lower alkyl)-benzenes (solvent) | ad 1000 ml |

The active substance and the two emulsifiers are dissolved in the solent at room temperature. After dilution with water the thus-obtained emulsifiable concentrate gives an emulsion which is very suitable as a spray liquor.

EXAMPLE 9

A spray powder has the following composition:

|  | Weight percent |
|---|---|
| Compound of formula I (active substance) | 50 |
| Sodium lauryl sulphate (wetting/dispersing agent) | 1 |
| Sodium lignosulphonate (dispersing agent) | 2 |
| Hydrated silicic acid (about 87% SiO$_2$) (inert pulverous carrier substances) | 5 |
| Kaolin (mainly Al$_2$(Si$_2$O$_5$)(OH)$_4$) | 42 |
|  | 100 |

The active substance is mixed homogeneously with the remaining formulation components in a suitable apparatus. The resulting powder is then finely ground in a suitable milling aggregate (e.g. pin, hammer, ball or air-jet mill) to a particle size which is required for an optimum biological activity and thereafter again mixed. The resulting spray powder is spontaneously wetted with water and gives well-suspended, ready-for-use spray liquors.

What is claimed is:

1. A compound for the control of mites and insects of the species Homoptera, of the formula

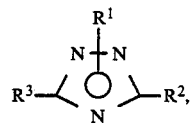

wherein
R$^1$ is attached to the 1- or 2-position of the 1,2,4-triazole ring and is methyl, ethyl or C$_{1-4}$-haloalkyl;
R$^2$ is o-halophenyl, o,o'-dihalophenyl or o,p-dihalophenyl, which halogen atoms are selected from the group consisting of fluorine, chlorine, bromine and iodine atoms; or phenyl which is substituted in the ortho position with a methyl, trifluoromethyl, methoxy or cyano group; and
R$^3$ is o-trifluoromethyl-phenyl, or an acid addition salt of such a compound.

2. The compound of claim 1 wherein R$^1$ is situated in the position adjacent to group R$^3$.

3. The compound of claim 1 wherein R$^1$ is methyl or ethyl.

4. The compound of claim 1 wherein R$^2$ is o-halophenyl or o,o'-dihalophenyl.

5. The compound of claim 1 wherein R$^2$ is o,p-dihalophenyl.

6. The compound of claim 1, selected from the group consisting of:
3-(o-chlorophenyl)-1-methyl-5-(o-trifluoromethyl-phenyl)-1H-1,2,4-triazole and mixtures of this compound with 5-(o-chlorophenyl)-1-methyl-3-(o-trifluoromethylphenyl)-1H-1,2,4-triazole,
3-(o,o'-difluorophenyl)-1-methyl-5-(o-trifluoromethylphenyl)-1H-1,2,4-triazole and mixtures of this compound with 5-(o,o'-difluorophenyl)-1-methyl-3-(o-trifluoromethyl-phenyl)-1H-1,2,4-triazole,
3-(o-bromophenyl)-1-methyl-5-(o-trifluoromethyl-phenyl)-1H-1,2,4-triazole,
3-(2-chloro-6-fluorophenyl)-1-methyl-5-(o-trifluoromethylphenyl)-1H-1,2,4-triazole,
3-(o,p-dichlorophenyl)-1-methyl-5-(o-trifluoromethyl-phenyl)-1H-1,2,4-triazole and
3-(2-chloro-4-fluorophenyl)-1-methyl-5-(o-trifluoromethylphenyl)-1H-1,2,4-triazole.

7. The compound of claim 1, selected from the group consisting of:
5-(o-fluorophenyl)-1-methyl-3-(o-trifluoromethyl-phenyl)-1H-1,2,4-triazole,
3-(o-fluorophenyl)-1-methyl-5-(o-trifluoromethyl-phenyl)-1H-1,2,4-triazole,
1-ethyl-5-(o-chlorophenyl)-3-(o-trifluoromethyl-phenyl)-1H-1,2,4-triazole,
1-ethyl-3-(o-chlorophenyl)-5-(o-trifluoromethyl-phenyl)-1H-1,2,4-triazole,
1-methyl-3,5-di(o-trifluoromethyl-phenyl)-1H-1,2,4-triazole, 1-methyl-3-(o-tolyl)-5-(o-trifluoromethyl-phenyl)-1H-1,2,4-triazole,
1-methyl-5-(o-tolyl)-3-(o-trifluoromethyl-phenyl)-1H-1,2,4-triazole,
1-ethyl-3-(o-fluorophenyl)-5-(o-trifluoromethyl-phenyl)-1H-1,2,4-triazole,
1-ethyl-5-(o-fluorophenyl)-3-(o-trifluoromethyl-phenyl)-1H-1,2,4-triazole,
3-(o,o'-dichlorophenyl)-1-methyl-5-(o-trifluoromethyl-phenyl)-1H-1,2,4-triazole,
3-(o-anisyl)-1-methyl-5-(o-trifluoromethyl-phenyl)-1H-1,2,4-triazole,
3-(o-chlorophenyl)-1-(2,2,2-trifluoroethyl)-5-(o-trifluoromethyl-phenyl)-1H-1,2,4-triazole,
3-(o-iodophenyl)-1-methyl-5-(o-trifluoromethyl-phenyl)-1H-1,2,4-triazole,
3-(o,p-difluorophenyl)-1-methyl-5-(o-trifluoromethyl-phenyl)-1H-1,2,4-triazole,
3-(4-chloro-2-fluorophenyl)-1-methyl-5-(o-trifluoromethyl-phenyl)-1H-1,2,4-triazole,
3-(o-cyanophenyl)-1-methyl-5-(o-trifluoromethyl-phenyl)-1H-1,2,4-triazole and
1-(2-chloroethyl)-3-(o-chlorophenyl)-5-(o-trifluoromethylphenyl)-1H-1,2,4-triazole.

8. The compound of claim 1, selected from the group consisting of:
3-(o-trifluoromethyl-phenyl)-1-methyl-5-(o,o'-difluorophenyl)-1H-1,2,4-triazole and
1-ethyl-3-(o,o'-difluorophenyl)-5-(o-trifluoromethyl-phenyl)-1H-1,2,4-triazole.

9. A composition for the control of mites and insects of the species Homoptera comprising an effective amount of at least one compound of the formula

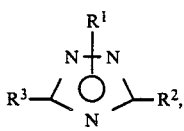

wherein
R$^1$ is attached to the 1- or 2-position of the 1,2,4-triazole ring and is methyl, ethyl or C$_{1-4}$-haloalkyl;
R$^2$ is o-halophenyl, o,o'-dihalophenyl or o,p-dihalophenyl, which halogen atoms are selected from the group consisting of fluorine, chlorine, bromine and iodine atoms; or phenyl which is substituted in the ortho position with a methyl, trifluoromethyl, methoxy or cyano group; and
R$^3$ is o-trifluoromethyl-phenyl, or an acid addition salt thereof; and formulation adjuvants.

10. The composition of claim 9, comprising an effective amount of at least one compound selected from the group consisting of:
3-(o-chlorophenyl)-1-methyl-5-(o-trifluoromethyl-phenyl)-1H-1,2,4-triazole,
5-(o-chlorophenyl)-1-methyl-3-(o-trifluoromethyl-phenyl)-1H-1,2,4-triazole,
3-(o,o'-difluorophenyl)-1-methyl-5-(o-trifluoromethyl-phenyl)-1H-1,2,4-triazole,
5-(o,o'-difluorophenyl)-1-methyl-3-(o-trifluoromethyl-phenyl)-1H-1,2,4-triazole,
3-(o-bromophenyl)-1-methyl-5-(o-trifluoromethyl-phenyl)-1H-1,2,4-triazole,
3-(2-chloro-6-fluorophenyl)-1-methyl-5-(o-trifluoromethyl-phenyl)-1H-1,2,4-triazole,
3-(o-p-dichlorophenyl)-1-methyl-5-(o-trifluoromethyl-phenyl)-1H-1,2,4-triazole, and
3-(2-chloro-4-fluorophenyl)-1-methyl-5-(o-trifluoromethyl-phenyl)-1H-1,2,4-triazole; and formulation adjuvants.

11. A method for the control of mites and insects of the species Homoptera, which method comprises treating a locus to be protected or such mites and insects with an effective amount of the compound of claim 1.

12. A method for the control of mites and insects of the species Homoptera, which method comprises treating, a locus to be protected or such mites and insects with an effective amount of the compound of claim 6.

13. A method for the control of mites and insects of the species Homoptera, which method comprises treating a locus to be protected or such mites and insects with an effective amount of the compound of claim 7.

14. A method for the control of mites and insects of the species Homoptera, which method comprises treating a locus to be protected or such mites and insects with an effective amount of the compound of claim 8.

15. A method for the control of mites and insects of the species Homoptera, which method comprises treating a locus to be protected or such mites and insects with an effective amount of the composition of claim 9.

16. A method for the control of mites and insects of the species Homoptera, which method comprises treating a locus to be protected or such mites and insects with an effective amount of the composition of claim 10.

* * * * *